US012649717B2

(12) United States Patent
Chen et al.

(10) Patent No.: US 12,649,717 B2
(45) Date of Patent: Jun. 9, 2026

(54) CYANINE-DERIVED COMPOUND, PREPARATION METHOD THEREFOR, AND APPLICATION THEREOF

(71) Applicant: Nanjing Genvivo Biotech Co., Ltd., Nanjing (CN)

(72) Inventors: Zhixing Chen, Nanjing (CN); Zhongtian Yang, Nanjing (CN); Liuju Li, Nanjing (CN)

(73) Assignee: Nanjing Genvivo Biotech Co., Ltd., Nanjing (CN)

( * ) Notice: Subject to any disclaimer, the term of this patent is extended or adjusted under 35 U.S.C. 154(b) by 650 days.

(21) Appl. No.: 17/789,659

(22) PCT Filed: May 24, 2021

(86) PCT No.: PCT/CN2021/095509

§ 371 (c)(1),
(2) Date: Dec. 16, 2022

(87) PCT Pub. No.: WO2021/244345

PCT Pub. Date: Dec. 9, 2021

(65) Prior Publication Data

US 2023/0174479 A1 Jun. 8, 2023

(30) Foreign Application Priority Data

Jun. 2, 2020 (CN) ......................... 202010492298.8

(51) Int. Cl.

| | |
|---|---|
| ***C07D 209/08*** | (2006.01) |
| ***C07D 209/60*** | (2006.01) |
| ***C09K 11/06*** | (2006.01) |
| ***G01N 21/64*** | (2006.01) |

(52) U.S. Cl.

CPC ......... *C07D 209/08* (2013.01); *C07D 209/60* (2013.01); *C09K 11/06* (2013.01); *C09K 2211/1018* (2013.01); *G01N 2021/6439* (2013.01)

(58) Field of Classification Search

CPC .... C07D 209/08; C07D 209/60; C09K 11/06; C09K 2211/1018; C09K 2211/1007; C09K 2211/1029; G01N 2021/6439; G01N 21/6428; G01N 21/6486

See application file for complete search history.

(56) References Cited

U.S. PATENT DOCUMENTS

| | | | | |
|---|---|---|---|---|
| 2003/0185756 | A1* | 10/2003 | Achilefu | A61K 49/0056 514/393 |
| 2015/0011731 | A1* | 1/2015 | Blanchard | C09B 23/083 536/23.1 |
| 2016/0263249 | A1* | 9/2016 | Frangioni | C09B 23/086 |

OTHER PUBLICATIONS

Zheng et al. (Chem. Sci., 2017, 8, 755-762, S1-S90).*

* cited by examiner

*Primary Examiner* — Robert H Havlin

(74) *Attorney, Agent, or Firm* — Nitin Kaushik

(57) ABSTRACT

Disclosed are a cyanine-derived compound, a preparation method therefor, and application thereof. The compound has the structure represented by formula (1), and the preparation method for the compound is further disclosed. The series of compounds of the present invention can be used as fluorescent markers for live-cell imaging analysis or flow cytometric analysis, solving problems of high toxicity, high cost and poor imaging effect of current.

(1)

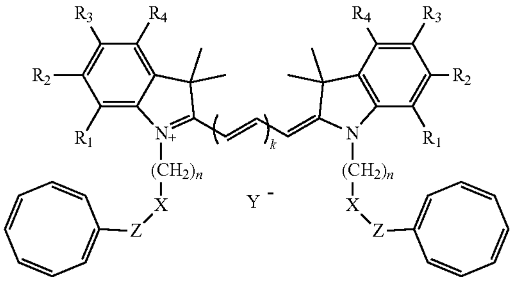

8 Claims, 4 Drawing Sheets

CYANINE-DERIVED COMPOUND, PREPARATION METHOD THEREFOR, AND APPLICATION THEREOF

CROSS-REFERENCE TO RELATED APPLICATION

This application is a National Stage Application of International Application No. PCT/CN2021/095509, filed on May 4, 2021, which claims priority to Chinese Patent Application No. 202010492298.8, filed on Jun. 2, 2020 and entitled "CYANINE-DERIVED COMPOUND, PREPARATION METHOD THEREFOR, AND APPLICATION THEREOF", the disclosure of which is herein incorporated by reference in its entirety.

TECHNICAL FIELD

The present invention belongs to the field of biological analysis, and in particular, relates to a cyanine-derived compound, a preparation method therefor, and application thereof in biological imaging analysis and flow cytometric analysis for mitochondria.

BACKGROUND

Mitochondrion, as an organelle in most of eukaryotic cells, is an essential energy generator for cells, and also plays an important role in other cellular processes such as cell signal transduction and apoptosis. Mitochondrion has a double-layered membrane structure, varies in shape in different types of cells and in different stages of a cell cycle, and has a more complex interaction with other organelles. Hence, the study on mitochondria depends on the development of live-cell imaging and analysis techniques, and the live-cell mitochondrial microscopic imaging depends on the development of novel mitochondrial fluorescent probes and novel microscopic imaging techniques. In recent years, with the application of super-resolution imaging techniques to life science researches, a variety of super-resolution microscopes, such as STED, SIM, and STORM microscopes, have been applied to in vivo mitochondrial imaging to achieve a series of results. Meanwhile, some defects of existing commercial fluorescent mitochondrial dyes are also highlighted.

At present, mainstream commercially-available fluorescent mitochondrial dyes are represented by MitoTracker® series dyes (U.S. Pat. No. 6,291,203) developed by Molecular Probes®. Most of these dyes are cyanine structured derivatives, and are accumulated in the mitochondria by virtue of positive charges carried by themselves to be fluorescent under an imaging condition. However, in super-resolution imaging or more sensitive cell imaging, these dyes often develop a large number of triplet states under high light intensity to induce the production of reactive oxygen species (ROS), which then interfere with the normal physiological activities of cells, resulting in manifestations of mitochondria deformation, rounding and swelling in mitochondrial imaging. As a result, the application of these dyes in the live-cell imaging is restricted. Therefore, the super-resolution live-cell imaging puts forward a higher requirement for the fluorescent mitochondrial dyes. Existing mitochondrial dyes have many defects such as high toxicity, high cost and poor imaging effect, and cannot meet the requirements of an imaging experiment with more demanding conditions, longer time, and higher light intensity.

SUMMARY

In view of the above defects in the prior art, the present invention provides a cyanine-derived compound as a mitochondrial fluorescent probe to solve the problems of high toxicity, high cost and poor imaging effect of current fluorescent mitochondrial dyes.

An object of the present invention is achieved by the following technical solution. A cyanine-derived compound provided by the present invention has a structure represented by formula (1):

(1)

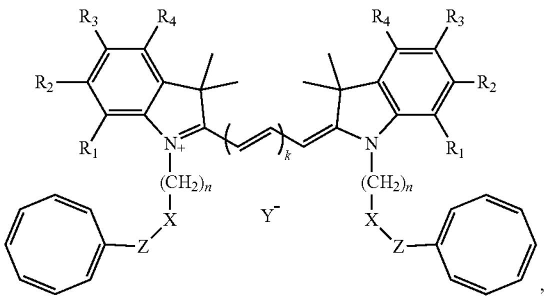

wherein n is an integer of at least 1;

k is an integer of 1-3;

$R_1$, $R_2$, $R_3$, and $R_4$ represent hydrogen, halogen, substituted or unsubstituted alkyl, substituted or unsubstituted alkoxy, substituted or unsubstituted aryl, ester or sulfonate, or any two adjacent substituents of $R_1$, $R_2$, $R_3$, and $R_4$, together with a carbon atom bonded thereto, form an unsubstituted or substituted aliphatic ring, aromatic ring or heteroaromatic ring, and the substituent is selected from halogen, alkyl, and alkoxy;

X is selected from —O— or —NH—;

Z is selected from —C(O)— or $-(CH_2)_m-$;

m is an integer of 1-6; and $Y^-$ is a biocompatible anion.

Preferably, the cyanine-derived compound of the present invention has a structure represented by formula (1a):

(1a)

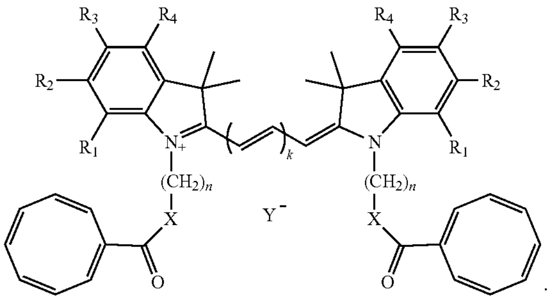

Preferably, n is an integer of 1-20, preferably, an integer of 1-10, and more preferably an integer of 1-6.

Preferably, $R_1$, $R_2$, $R_3$, and $R_4$ independently represent hydrogen, halogen, substituted or unsubstituted $C_{1-20}$ alkyl, substituted or unsubstituted $C_{1-20}$ alkoxy, substituted or unsubstituted $C_{6-30}$ aryl, $C_{1-20}$ ester or sulfonate, or any two adjacent substituents of $R_1$, $R_2$, $R_3$, and $R_4$, together with a carbon atom bonded thereto, form an unsubstituted or substituted $C_{3-10}$ aliphatic ring, $C_{6-30}$ aromatic ring or $C_{1-30}$ heteroaromatic ring, and the substituent is selected from halogen, $C_{1-20}$ alkyl, and $C_{1-20}$ alkoxy.

Preferably, $R_1$, $R_2$, $R_3$, and $R_4$ independently represent hydrogen, halogen, substituted or unsubstituted $C_{1-6}$ alkyl, substituted or unsubstituted $C_{1-6}$ alkoxy, substituted or unsubstituted $C_{6-18}$ aryl, $C_{1-6}$ ester or sulfonate, or any two adjacent substituents of $R_1$, $R_2$, $R_3$, and $R_4$, together with a carbon atom bonded thereto, form an unsubstituted or substituted $C_{3-10}$ aliphatic ring, $C_{6-18}$ aromatic ring or $C_{1-18}$ heteroaromatic ring, and the substituent is selected from halogen, $C_{1-6}$ alkyl, and $C_{1-6}$ alkoxy.

Preferably, the aryl is selected from phenyl.

Preferably, Z represents —C(O)-(carbonyl).

Preferably, Z represents $-(CH_2)_m-$, and m is an integer of 1-3.

Preferably, $Y^-$ is a bromine ion, a chlorine ion, or an acetate ion.

The cyanine derivative of the present invention is preferably of one of the following structures:

(1-1)

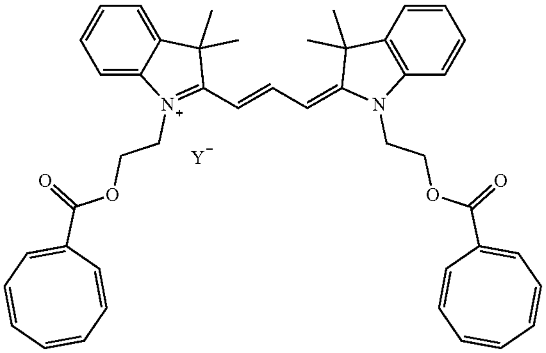

(1-2)

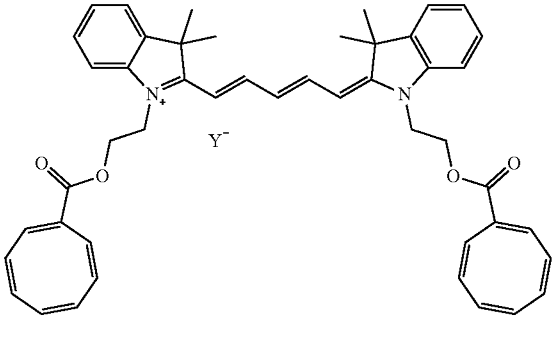

(1-3)

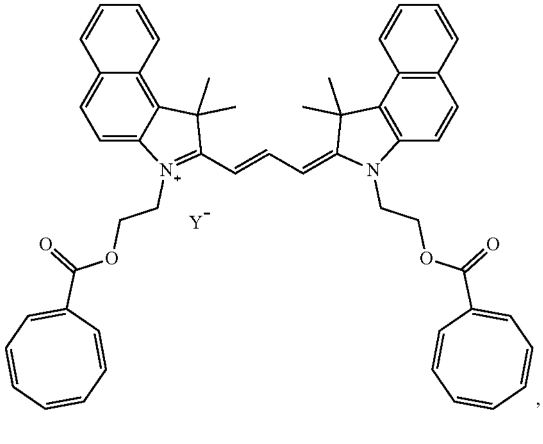

, wherein $Y^-$ is as previously defined.

The cyanine derivative of the present invention is one preferably selected from the following compounds:

(1-4)

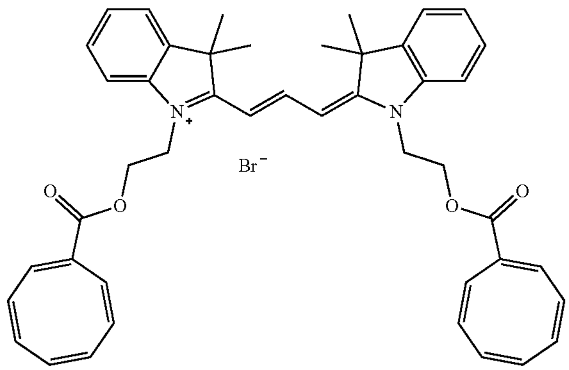

(1-5)

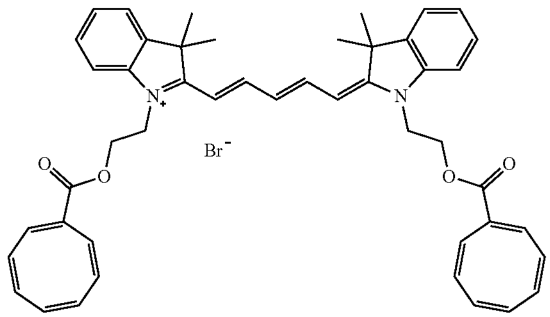

(1-6)

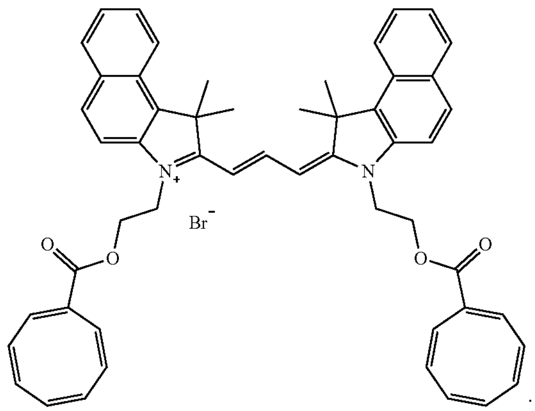

.

The present invention further provides a preparation method for a cyanine-derived mitochondrial fluorescent probe, including: performing an alkylation reaction on a compound of formula (2) as a raw material and a compound of formula (3) to obtain a compound of formula (4); then, performing a condensation reaction on the compound of formula (4) and a compound of formula (5) to obtain a compound of formula (6); and finally, deacetylating the compound of formula (6) to obtain a product, and then performing an esterification reaction on the product and cyclooctetetraenoic formic acid to obtain a biscyclooctetetraenoic-derived cyanine compound, namely, the compound of formula (1). A reaction route is shown as follows:

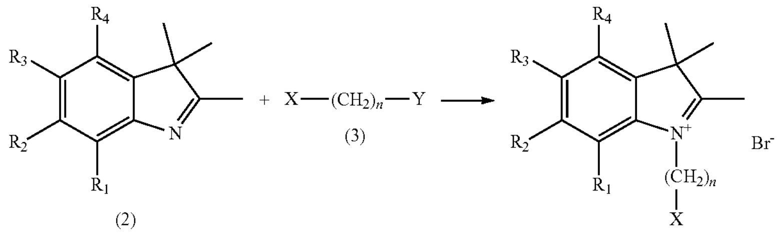

(2) (3) (4)

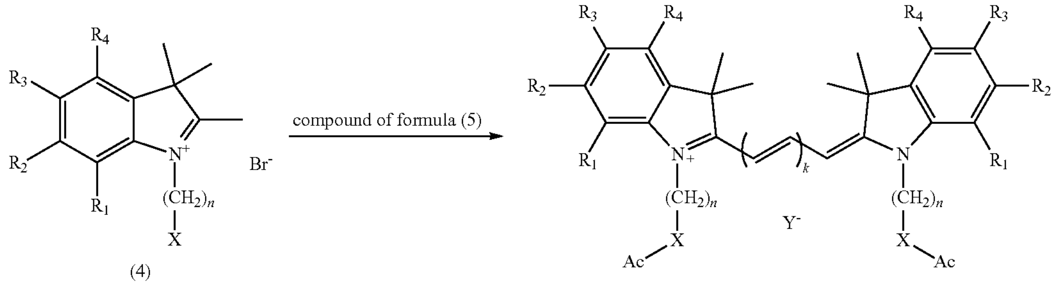

(4) (6)

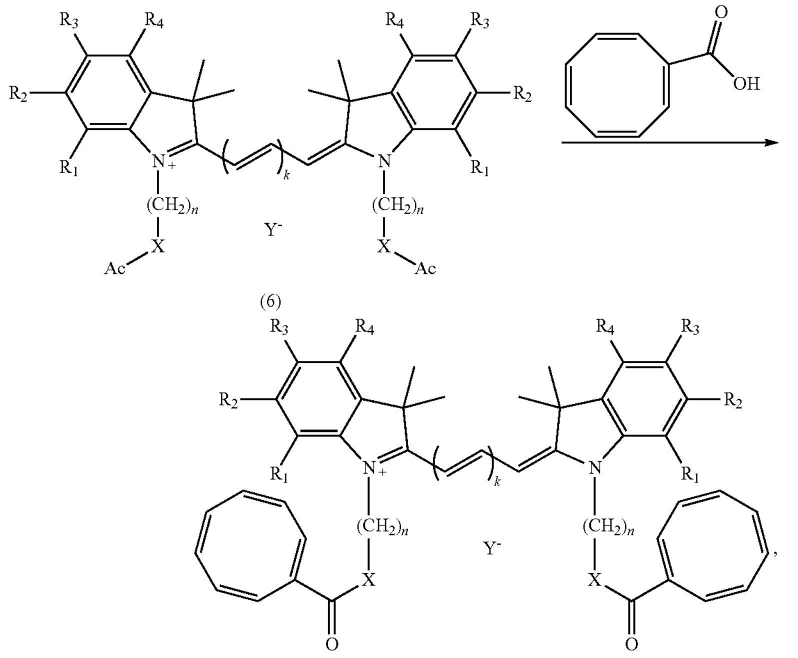

(6)

(1)

wherein when k=1, the compound represented by formula (5) is triethyl orthoformate, and when k=2 or 3, the compound of formula (5) is:

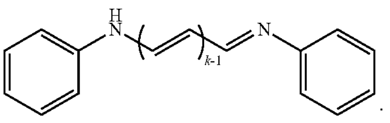

Preferably, a reaction solvent for the alkylation reaction is acetonitrile or toluene.

Preferably, the reaction temperature of the alkylation reaction is 100-150° C., more preferably 110° C.

Preferably, in the alkylation reaction, a molar ratio of the compound of formula (2) to the compound of formula (3) is 1:1.5.

Preferably, a reaction solvent for the condensation reaction is acetic anhydride, with sodium acetate as a catalyst.

Preferably, the reaction temperature of the condensation reaction is 100-150° C., more preferably 140° C.

Preferably, in the condensation reaction, a molar ratio of the compound of formula (4) to the compound of formula (5) is 2:1.

Preferably, the compound of formula (4) is deacetylated in methanol and sodium hydroxide.

Preferably, the esterification reaction occurs under the catalysis of 2-(7-Azabenzotriazol-1-yl)-N,N,N',N'-tetramethyluronium hexafluorophosphate (HATU) and triethylamine.

Preferably, a reaction solvent for the esterification reaction is DMF.

Preferably, the reaction temperature of the esterification reaction is 15-40° C., more preferably room temperature.

Preferably, in the esterification reaction, a molar ratio of the compound of formula (6) to the cyclooctetetraenoic formic acid is 1:2.5.

The method specifically includes the followings.

(1) Alkylation Reaction

The temperature of the alkylation reaction is 110° C., a reaction solvent is acetonitrile or toluene, and the reaction occurs in a sealed tube. A molar ratio of the compound of formula (2) to the compound of formula (3) during the reaction is 1:1.5.

(2) Condensation Reaction

A solvent for the condensation reaction is acetic anhydride, with sodium acetate as a catalyst under the reaction temperature of 140° C. A molar ratio of the compound of formula (4) to the compound of formula (5) is 2:1.

(3) Deacetylation and Esterification Reaction

The compound of formula (4) is deacetylated in methanol-sodium hydroxide to obtain a product, and then the esterification reaction is performed on the product and cyclooctetetraenoic formic acid under the catalysis of HATU and triethylamine. A reaction solvent is DMF, and the reaction temperature is room temperature. In the esterification reaction, a molar ratio of the compound of formula (6) to the cyclooctetetraenoic formic acid is 1:2.5.

The present invention further provides use of the compound of formula (1) as a mitochondrial fluorescent marker. The compound of formula (1) can be incubated to enter a mitochondrion of a live cell (including a subcultured cell such as a HeLa cell and a primary cell such as a cardiomyocyte), and is fluorescent in the presence of exciting light, thereby acting as a probe for living-cell fluorescence imaging analysis or flow cytometric analysis.

Typical application steps include the followings.

(1) Incubation of Cells and Probes

A solution of probes at a certain concentration in a cell culture medium is prepared, and cells are incubated with the solution for a certain period of time under a standard cell culture condition. After a certain period of incubation, the solution of probes is removed, and residues are washed away with a new culture medium.

(2) Performing Imaging Experiment or Flow Analysis Experiment

In step (1), the concentration of the probes is 50-250 nM, and an incubation time is 10-20 min.

The phototoxicity of the probes 1-4, 1-5, and 1-6 of the present invention and the phototoxicity of existing commercial probes are determined by measuring the cell viability after irradiating the cells continuously under high light intensity. Results show that the probes of the present invention are relatively lower in phototoxicity than that of the existing commercial mitochondrial probes MTR CMXRos and MTDR. Compared with the existing commercial mitochondrial probes MTR CMXRos and MTDR, the probes 1-4, 1-5, and 1-6 of the present invention are about 5 times less phototoxic than MTR CMXRos, MTDR and non-optimized compounds of 1-6.

Compared with the prior art, the present invention has the following advantages.

(1) The triplet-state quenching effect of double protective groups significantly reduces the toxic species generated via the triplet state of dye under a microscope light source during various microscopic imaging processes, which almost truly presents the closest physiological activities of the cells themselves;

(2) Compared with the existing commercial mitochondrial probes, the present invention shows less toxicity and phototoxicity to cells, with optimal overall biocompatibility, which can allow imaging experiments with more demanding conditions, longer time, and higher light intensity.

(3) In the flow cytometric analysis and sorting using mitochondria as fluorescent markers, the present invention can reduce the cell damage caused by the toxicity and phototoxicity of a previous commercial dye, and maintain the physiological activity of the sorted cells.

(4) The present invention has readily available raw materials, low cost, and simple reaction conditions, showing commercial advantages.

DETAILED DESCRIPTION

Embodiment 1 Synthesis of Fluorescent Probe

Figure 1:
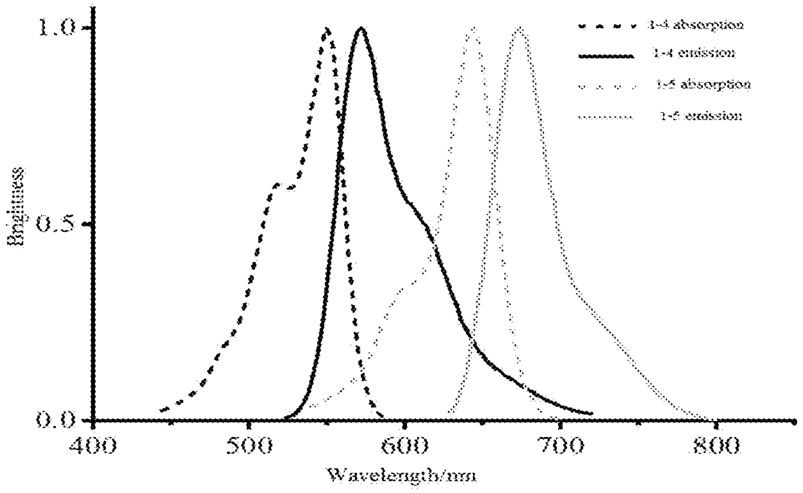
FIG. 1 shows normalized absorption and emission spectra, in methanol, of compounds of formula (1-4) and formula (1-5) synthesized in Embodiment 1 of the present invention.

All water-sensitive and air-sensitive reactions were carried out in a nitrogen atmosphere under an anhydrous condition. The reactions were monitored by thin-layer chromatography (TLC, GF254) under UV light by using a solution of phosphomolybdic acid and cerium sulfate in ethanol, as a visualizer. Compounds were isolated by silica gel flash column chromatography, unless otherwise specified. The nuclear magnetic resonance (NMR) spectra of the compounds were measured by a Bruker Advance 400 ($^1$H 400 MHz) NMR spectrometer and calibrated with a residual undeuterated solvent (in $^1$H NMR, 7.26 ppm deuterated chloroform, and 3.31 ppm methanol-$d_4$). The following abbreviations were used to explain multiplicity: s=singlet, d=doublet, t=triplet, q=quartet, m=multiplet, br=broad peak. Mass spectrometry data were acquired by using Acquity I class UPLC synapt G2-SI and electrospray ionization (ESI).

Embodiment 1-1. In the general formula (1) of the present invention, when n=2, k=1, X is O, and $R_1$-$R_4$ are hydrogen, the compound of this embodiment has the structure represented by formula (1-4), namely a probe 1-4, the preparation method of which was as follows.

7.1 g of 2-bromoethanol and 3 g of 2,3,3-Trimethylindolenine were mixed and dissolved in 50 ml of DMF, and heated and stirred at 110° C. for 12 hours to obtain a reaction mixture. After the reaction mixture was cooled to room temperature, a white solid was precipitated. The white solid was filtered by suction and washed with ether to obtain 2.5 g of a compound of formula (7) with the purity of 46%.

$^{1}$H NMR (400 MHz, Methanol-$d_4$) δ 7.90-7.82 (m, 1H), 7.82-7.74 (m, 1H), 7.70-7.59 (m, 2H), 4.70-4.63 (t, J=5.1 Hz, 2H,), 4.08-4.01 (t, J=5.1 Hz, 2H), 1.62 (s, 6H).

(7)

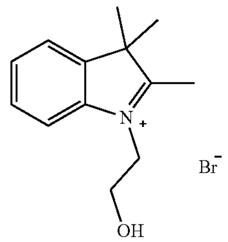

200 mg of the compound of formula (7) and 133 mg of triethyl orthoformate were heated to 110° C. in 5 ml of acetic anhydride, stirred and reacted for 2 hours to obtain a reaction mixture. The reaction mixture was spin-dried and purified by HPLC to obtain 180 mg of a compound of formula (8).

$^{1}$H NMR (400 MHz, Methanol-$d_4$) δ 8.60 (t, J=13.4 Hz, 1H), 7.58-7.51 (m, 2H), 7.45 (ddd, J=8.3, 7.1, 1.2 Hz, 2H), 7.44-7.37 (m, 2H), 7.32 (td, J=7.3, 1.2 Hz, 2H), 6.60 (d, J=13.4 Hz, 2H), 4.60-4.54 (m, 4H), 4.54-4.46 (m, 4H), 1.83 (s, 6H), 1.77 (s, 12H).

$^{13}$C NMR (101 MHz, Methanol-$d_4$) δ 175.63, 170.84, 151.24, 142.20, 140.66, 128.46, 125.49, 122.14, 111.21, 102.84, 60.23, 49.39, 43.22, 26.81, 19.16.

HRMS (ESI) calcd for $C_{31}H_{37}N_2O_4^+$ [$M^+$] 501.2748, found 501.2753.

(8)

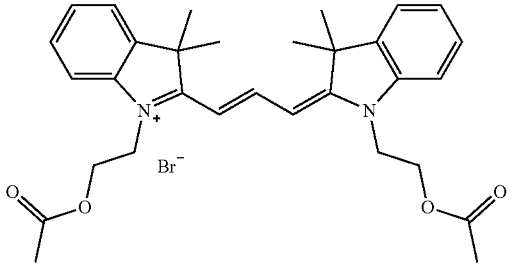

30 mg of the compound of formula (8) was dissolved in 2 ml of methanol, then, 15 mg of sodium hydroxide was added, and the reaction was carried out for 2 hours while stirring to obtain a mixture; and the mixture was evaporated under rotation to obtain a solid. The solid was mixed with 50 mg of 2-(7-Azabenzotriazol-1-yl)-N,N,N',N'-tetramethyluronium hexafluorophosphate (HATU), 10 mg of cyclooctetetraenoic formic acid (COTCOOH) and 20 μl of triethylamine in DMSO at room temperature to react for 12 hours. The reaction mixture was diluted with water, extracted three times with dichloromethane, and purified by HPLC to obtain 12 mg of a compound of formula (1-4).

$^{1}$H NMR (400 MHz, Methanol-$d_4$) δ 8.59 (t, J=13.4 Hz, 1H), 7.56 (d, J=7.5 Hz, 2H), 7.51-7.38 (m, 4H), 7.35 (t, J=7.4 Hz, 2H), 6.88 (s, 1H), 6.53 (d, J=13.4 Hz, 2H), 5.95-5.66 (m, 12H), 4.65 (t, J=5.0 Hz, 4H), 4.54 (t, J=5.2 Hz, 4H), 1.78 (s, 12H).

$^{13}$C NMR (101 MHz, Chloroform-d) δ 174.60, 165.25, 151.16, 143.54, 142.44, 140.28, 133.94, 132.94, 132.62, 132.02, 131.35, 130.04, 129.30, 128.88, 125.45, 122.02, 111.30, 104.52, 60.96, 49.15, 43.37, 28.09.

HRMS (ESI) calcd for $Ca_{45}H_{45}N_2O_4^+$ [$M^+$] 677.3374, found 677.3377.

(1-4)

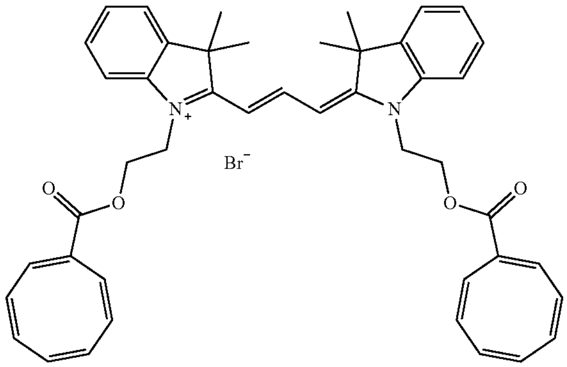

Embodiment 1-2. In the general formula (1) of the present invention, when n=2, k=2, and X is O, the compound of this embodiment has the structure represented by formula (1-5), namely a probe 1-5, the preparation method of which was as follows:

The compound of formula (7) was prepared with the same method as described above. 100 mg of the compound of formula (7) and 50 mg of N-(3-(phenylamino) allylidene) aniline hydrochloride were heated to 110° C. in 5 ml of acetic anhydride, then reaction was carried out for 2 hours while stirring to obtain a mixture; and the mixture was spin-dried and purified by HPLC to obtain 71 mg of the compound of formula (9).

$^{1}$H NMR (400 MHz, Methanol-$d_4$) δ 8.32 (t, J=13.0 Hz, 2H), 7.49 (dd, J=7.5, 1.2 Hz, 2H), 7.42 (td, J=7.7, 1.2 Hz, 2H), 7.34 (d, J=7.9 Hz, 2H), 7.27 (td, J=7.4, 1.0 Hz, 2H), 6.65 (t, J=12.4 Hz, 1H), 6.39 (d, J=13.7 Hz, 2H), 4.52 (t, J=5.1 Hz, 4H), 4.42 (t, J=5.1 Hz, 4H), 1.85 (s, 6H), 1.73 (s, 12H).

$^{13}$C NMR (101 MHz, Methanol-$d_4$) δ 174.30, 170.85, 154.67, 144.93, 142.28, 141.11, 128.23, 124.97, 122.03, 110.70, 103.40, 60.26, 49.30, 42.84, 26.43, 19.16.

HRMS (ESI) calcd for $C_{33}H_{39}N_2O_4^+$ [$M^+$] 527.2904, found 527.2915.

(9)

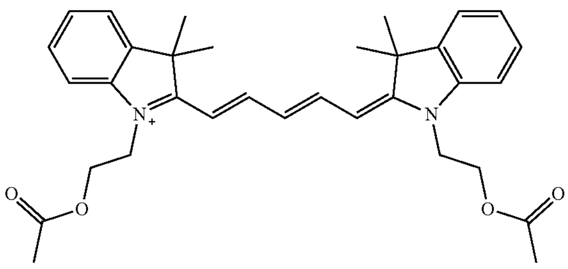

91 mg of the compound of formula (9) was dissolved in 5 ml of methanol, 45 mg of sodium hydroxide was added, and reaction was carried out for 2 hours while stirring to obtain a mixture; and the mixture was evaporated under rotation to obtain a solid. The solid was mixed with 50 mg of 2-(7-Azabenzotriazol-1-yl)-N,N,N',N'-tetramethyluronium hexafluorophosphate (HATU), 13 mg of cyclooctetetraenoic formic acid (COTCOOH) and 30 μl of triethylamine in DMSO at room temperature to react for 12 hours to obtain a reaction mixture. The reaction mixture was diluted with water, extracted three times with dichloromethane, and purified by HPLC to obtain 17 mg of a compound of formula (1-5).

$^1$H NMR (400 MHz, Methanol-$d_4$) δ 8.30 (t, J=13.1 Hz, 2H), 7.50 (d, J=7.5 Hz, 2H), 7.43 (t, J=7.7 Hz, 2H), 7.35 (d, J=8.0 Hz, 2H), 7.29 (t, J=7.4 Hz, 2H), 6.89 (s, 2H), 6.61 (t, J=12.4 Hz, 1H), 6.39 (d, J=13.7 Hz, 2H), 5.92-5.70 (m, 12H), 4.62 (t, J=5.0 Hz, 4H), 4.49 (t, J=5.1 Hz, 4H), 1.74 (s, 12H).

$^{13}$C NMR (101 MHz, Chloroform-d) δ 173.97, 165.30, 153.95, 143.97, 142.01, 141.09, 134.29, 133.38, 132.46, 132.03, 131.44, 129.94, 129.02, 128.59, 126.57, 125.37, 122.32, 60.61, 49.61, 43.01, 27.87.

HRMS (ESI) calcd for $C_{47}H_{47}N_2O_4^+$ [$M^+$] 703.3530, found 703.3520.

(1-5)

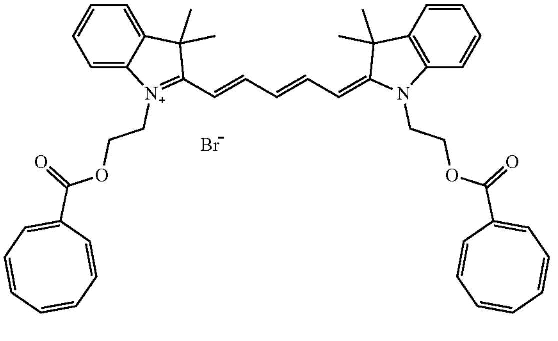

FIG. 1 shows the normalized absorption and emission spectra, in methanol, of the compounds of formula (1-4) and formula (1-5).

Embodiments 1-3 Preparation

The compound of formula (7) in the preparation method of Embodiment 1-1 was replaced with the compound of formula (7-1) to prepare the compound of formula (1-6), namely, a probe 1-6.

(7-1)

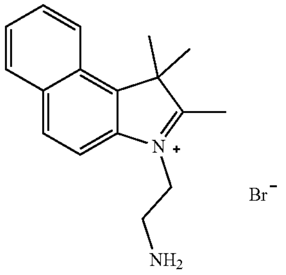

$^1$H NMR (400 MHz, Chloroform-d) δ 8.68 (t, J=13.1 Hz, 1H), 8.12 (d, J=8.4 Hz, 1H), 7.94 (dd, J=17.4, 8.5 Hz, 4H), 7.64 (ddd, J=8.3, 6.8, 1.3 Hz, 2H), 7.56 (d, J=13.2 Hz, 2H), 7.51 (ddd, J=8.0, 6.9, 1.0 Hz, 2H), 7.46 (d, J=8.8 Hz, 2H), 6.83 (s, 2H), 5.78 (s, 1H), 5.69-5.55 (m, 12H), 5.32 ((d, J=13.2 Hz, 4H), 4.84 (d, J=13.2 Hz, 4H), 2.06 (s, 12H).

HRMS (ESI $C_{53}H_{49}N_2O_4^+$ found 777.5654.

Meanwhile, the compound of formula (1-6-1) was synthesized as the control of phototoxicity experiment:

(1-6-1)

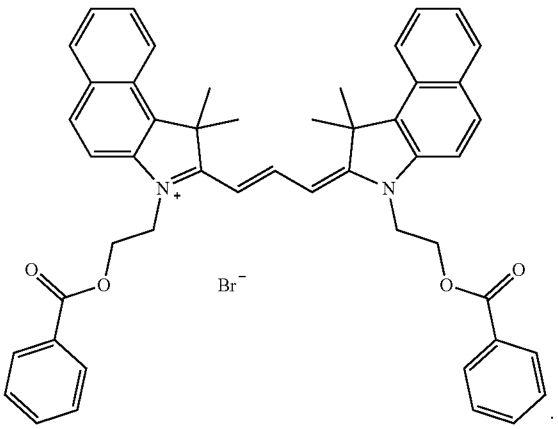

HRMS (ESI $C_{49}H_{45}N_2O_4^+$ found 725.4713.

Embodiment 2 Colocalization Experiment with Existing Commercial Probe

Figure 4:
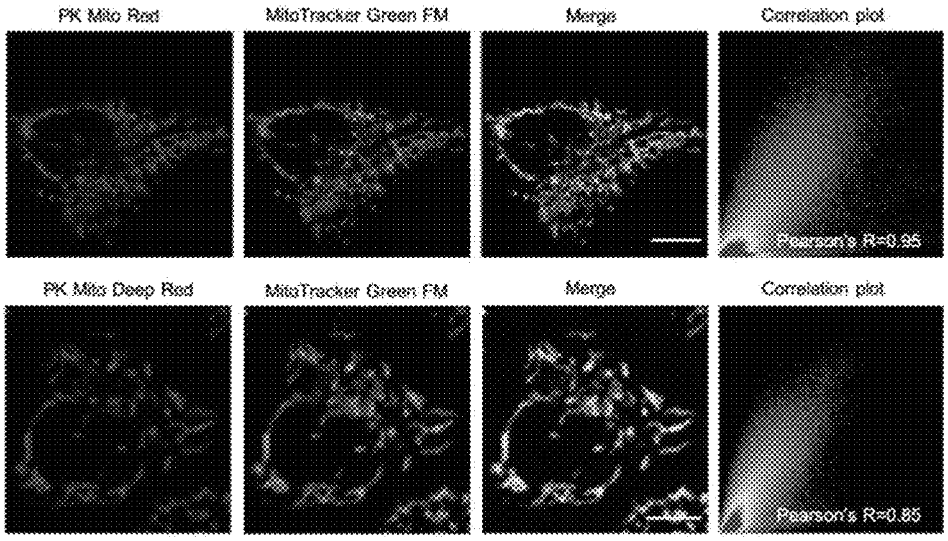
FIG. 4 shows a co-localization experiment of labeling mitochondria of HeLa cells with the compounds of formula (1-4) and formula (1-5) and the commercial dye MitoTracker green FM.

HeLa cells were stained for 15 minutes with 250 nM probe 1-4 or probe 1-5 and a commercial dye MitoTracker Green FM; the stains were washed off, and then a colocalization assay was carried out. As shown in FIG. 4, the probe provided by the present invention exhibited excellent co-localization with the commercial dye and can label the mitochondria effectively.

Figure 2:
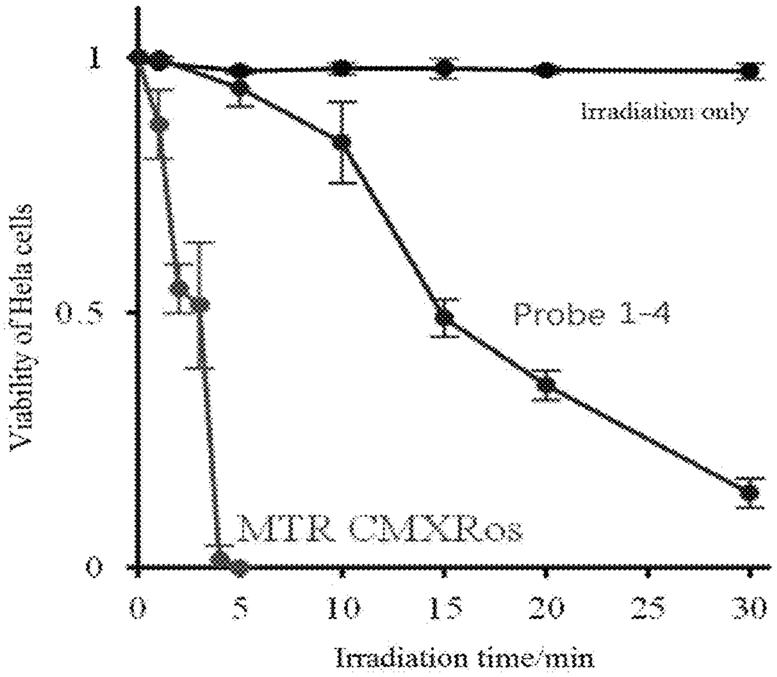
FIG. 2 shows a comparative data diagram of phototoxicity on HeLa cells between the compound of formula (1-4) and a commercial dye MitoTracker Red CMXRos (MTR CMXRos)
Figure 3:
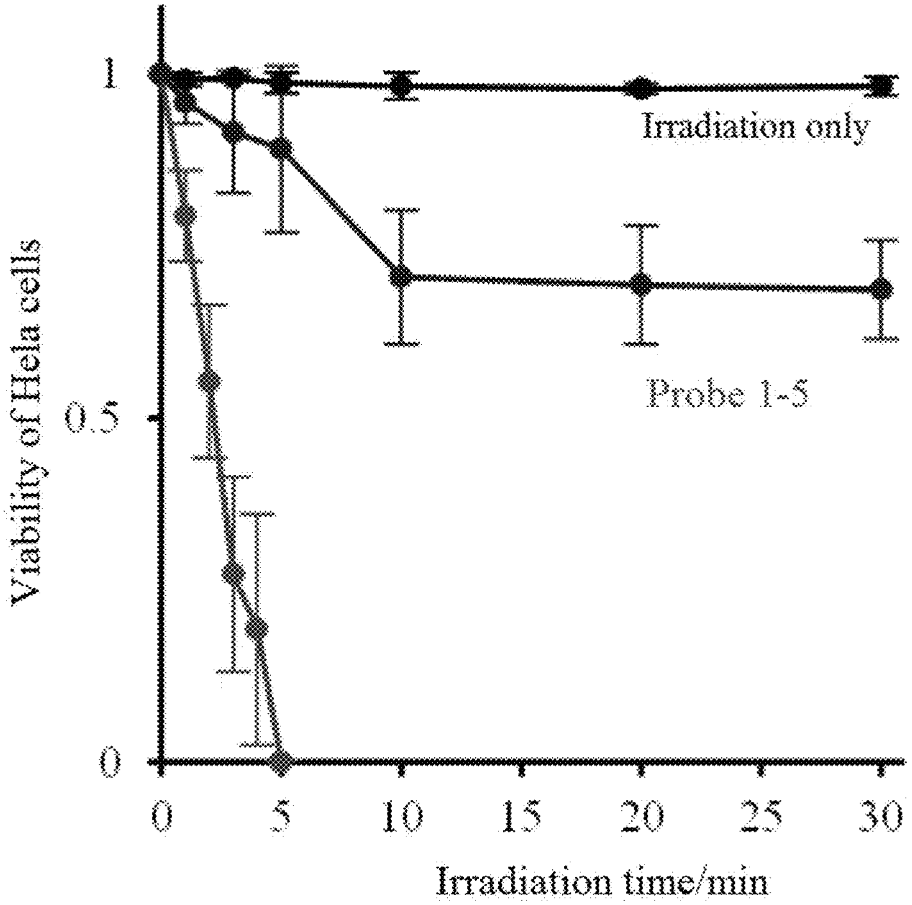
FIG. 3 shows a comparative diagram of phototoxicity on HeLa cells between the compound of formula (1-5) and a commercial dye MitoTracker Deep Red FM (MTDR)

Embodiment 3 Phototoxicity Assay of Probes Provided by the Present Invention and Existing Commercial Probes HeLa cells were irradiated with corresponding LED light (same light intensity for the same channel) for different periods of time under a widefield fluorescence microscope. The irradiated cells were incubated for 2 hours in a cell incubator at 37° C. Then, the cells were stained with propidium iodide (PI) for viability counting. As shown in FIG. 2 and FIG. 3, two types of probes, i.e., the probes 1-4 and 1-5, in Embodiment 1 were about five times less phototoxic than the commercial dyes in the HeLa cells.

Figure 5:
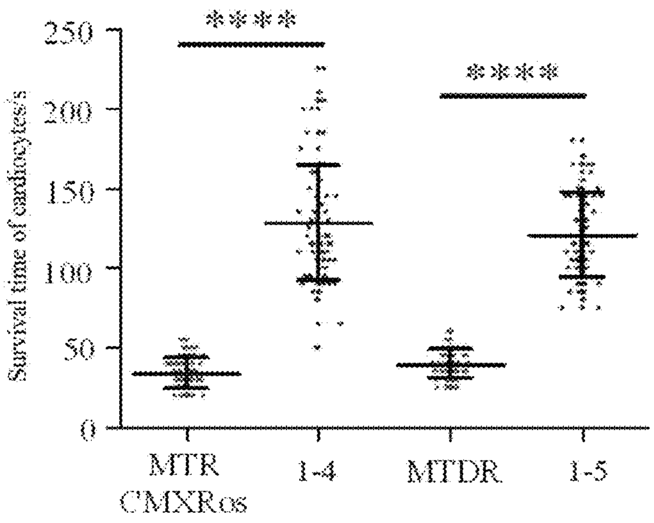
FIG. 5 shows a comparison diagram of phototoxicity on rat cardiomyocytes between the compounds of formula (1-4) and formula (1-5) and commercial dyes.

Rat cardiomyocytes were stained for 15 minutes with 250 nM probe provided by the present invention or commercial dye, and the dye was then washed off. The cells were re-covered with the culture medium, and were continuously irradiated and imaged with corresponding laser light in a high-throughput imaging system. Imaging results were analyzed, and the time of irreversible contraction of the cardiomyocytes was counted. As shown in FIG. 5, the probes 1-4 and 1-5 of the present invention were about five times less phototoxic than the commercial dye in the rat cardiomyocytes.

The probe 1-6 of the present invention and its reference compound of formula (1-6-1) were also subjected to phototoxicity comparison and determination according to the above steps. Results showed that the probe 1-6 of the present invention had an effect similar to those of the probes 1-4 and 1-5, but with lower phototoxicity. The phototoxicity data are listed in the table below

| | Cell viability under 1-minute irradiation | Cell viability under 5-minute irradiation | Cell viability under 15-minute irradiation |
|---|---|---|---|
| Probe 1-4 | 99.0% | 94.0% | 48.9% |
| MitoTracker Red CMXRos | 86.9% | 0% | 0% |
| Probe 1-5 | 100% | 86% | 69% |
| MitoTracker Deep Red FM | 100% | 0% | 0% |
| Probe 1-6 | 100% | 99% | 95% |
| 1-6-1 | 100% | 95% | 25% |

Figure 6:
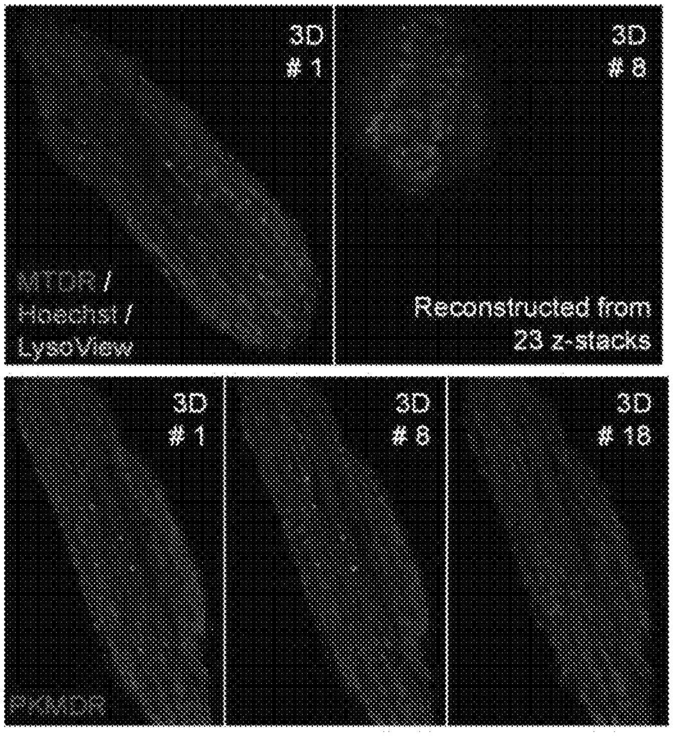
FIG. 6 shows experimental comparison data of 3D-laser confocal time-series imaging of rat cardiomyocytes labeled with the compound of formula (1-4) and the commercial dye MTR CMXRos.

Embodiment 4 Imaging Experiment on Cells with Probe Provided by the Present Invention Target cells were stained with 250 nM probe provided by the present invention and dye for 10-15 minutes, the dye was then washed off, and a corresponding culture medium was added. Then, different microscopic imaging experiments were carried out. FIG. 6 shows an experimental comparison of 3D-laser confocal time-series imaging of rat cardiomyocytes labeled with the probe 1-5 and the commercial dye MTDR. The cells labeled with the commercial dye violently contracted to death after 8 time sequences, whereas the same process occurred to the cells labeled with the present invention after 23 time sequences.

Figure 7:
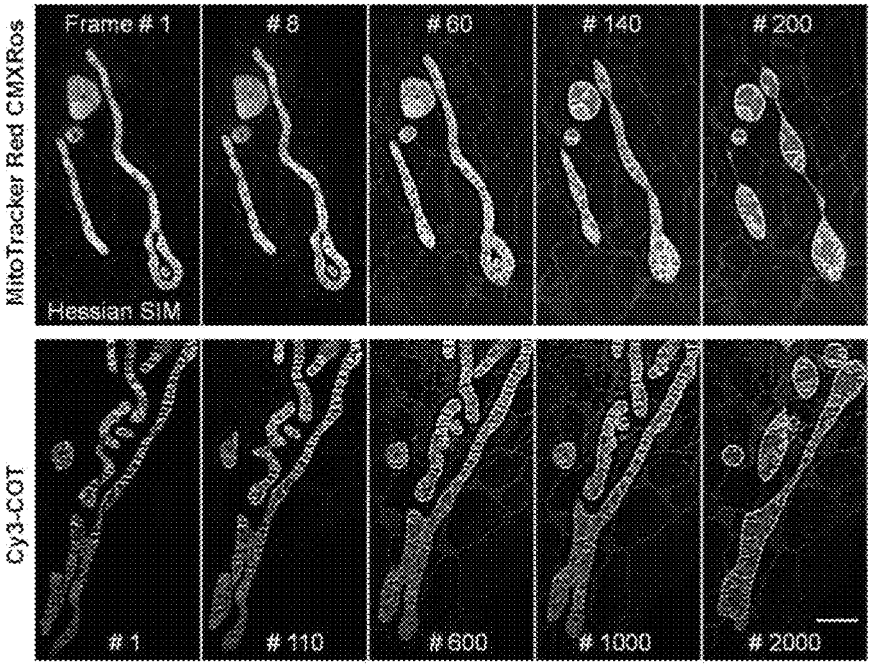
FIG. 7 shows a comparative data diagram of Hessian-SIM super-resolution mitochondrial imaging of COS7 cells labeled with the compound of formula (1-5) and the commercial dye MTDR.

FIG. 7 shows the comparison of Hessian-SIM super-resolution mitochondrial imaging of COS7 cells labeled with probe 1-4 versus the commercial dye MTDR. The MTDR-labeled mitochondria were already severely deformed and rounded at the 200th frame of imaging, whereas the similar process occurred to the probe 1-4 was still less severe than that of MTDR after 2000 frames of imaging.

What is claimed is:

1. A cyanine derivative, having a structure represented by formula (1):

(1)

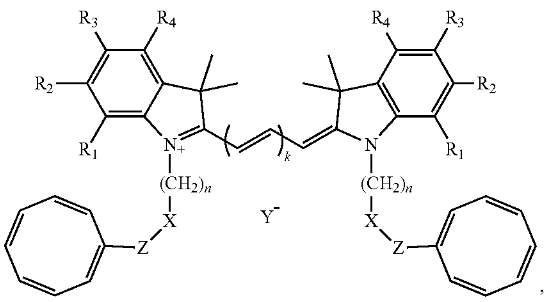

, wherein

X is selected from —O— or —NH—;

Z is selected from —C(O)— or —$(CH_2)_m$—;

$Y^-$ is a biocompatible anion bromine ion, a chlorine ion, or an acetate ion;

$R_1$, $R_2$, $R_3$, and $R_4$ are selected from hydrogen, halogen, substituted or unsubstituted $C_{1-20}$ alkyl, substituted or unsubstituted $C_{1-20}$ alkoxy, substituted or unsubstituted $C_{6-30}$ aryl, $C_{1-20}$ ester, or sulfonate, or any two adjacent groups of $R_1$, $R_2$, $R_3$, and $R_4$, together with a carbon atom bonded thereto, form an unsubstituted or substituted $C_{3-10}$ aliphatic ring, $C_{6-30}$ aromatic ring or $C_{1-30}$ heteroaromatic ring, wherein a substituent is selected from halogen, alkyl, and alkoxy;

n is an integer not less than 1;

k is an integer of 1-3; and m is an integer of 1-6.

2. The cyanine derivative according to claim 1, wherein Z is selected from —C(O)—.

3. The cyanine derivative according to claim 1, wherein $R_1$, $R_2$, $R_3$, and $R_4$ are each selected from hydrogen; n=2; X is —O—; Z is selected from —C(O)—; and Y is the bromine ion.

4. The cyanine derivative according to claim 1, wherein $R_1$ and $R_2$ are each selected from hydrogen; $R_3$ and $R_4$, together with the carbon atom bonded thereto, form phenyl; Z is selected from —C(O)—; and Y is the bromine ion.

5. A preparation method for a cyanine derivative of formula (1a) according to claim 1, comprising the following steps:

step 1, performing an alkylation reaction on a compound of formula (2) as a raw material and a compound of formula (3) to obtain a compound of formula (4):

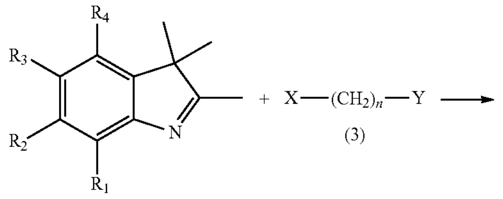

(2) (3)

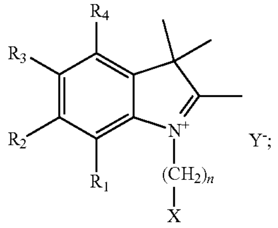

(4)

step 2, performing a condensation reaction on the compound of formula (4) and a compound of formula (5) to obtain a compound of formula (6):

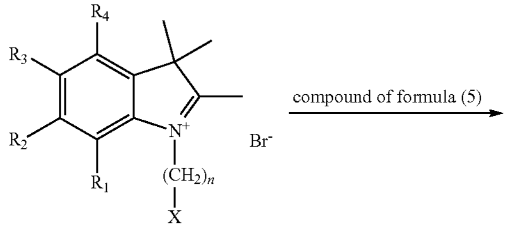

(4)

-continued

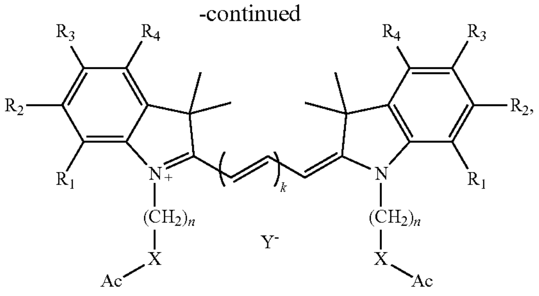

(6)

wherein when k=1, the compound represented by formula (5) is triethyl orthoformate, and when k=2 or 3, the compound of formula (5) is:

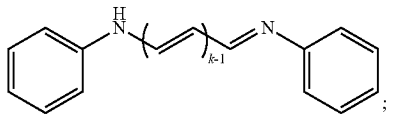

and step 3, deacetylating the compound of formula (6) to obtain a product, and then performing an esterification reaction on the product with cyclooctetetraenoic formic acid to obtain the cyanine derivative of formula (1a):

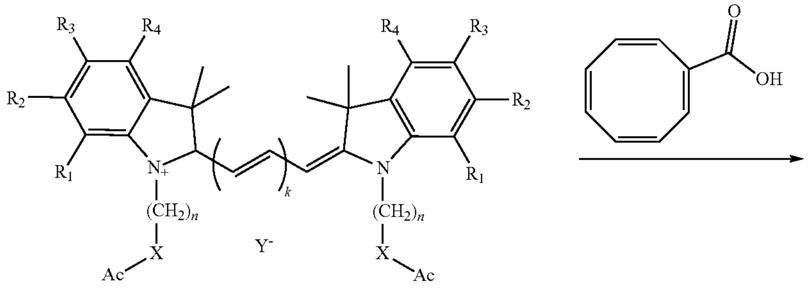

(6)

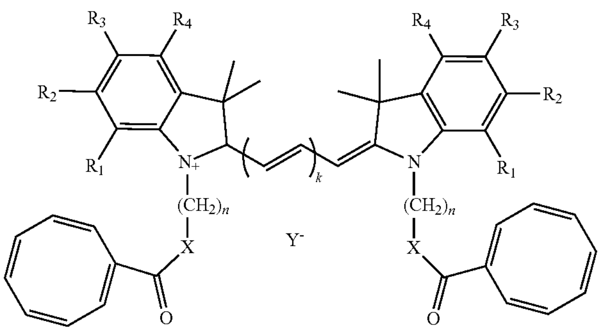

(1a)

6. The preparation method for the cyanine derivative according to claim 5, wherein a solvent used in the alkylation reaction of step 1 is toluene or acetonitrile; a solvent used in the condensation reaction of step 2 is acetic anhydride, with sodium acetate as a catalyst; and catalysts for the esterification reaction of step 3 are 2-(7-Azabenzotriazol-1-yl)-N,N,N',N'-tetramethyluronium hexafluorophosphate HATU and triethylamine, with DMF as a solvent.

7. The preparation method for the cyanine derivative according to claim 5, wherein a molar ratio of the compound of formula (2) to the compound of formula (3) in the alkylation reaction is 1:1.5; a molar ratio of the compound of formula (4) to the compound of formula (5) in the condensation reaction is 2:1; and a molar ratio of the compound of formula (6) to the cyclooctetetraenoic formic acid in the esterification reaction is 1:2.5.

8. Application of the cyanine derivative according to claim 1 as a mitochondrial fluorescent marker for live-cell imaging analysis or flow cytometric analysis by incubating compound of formula (1) with live cells to enter a mitochondrion of the live cells and performing live-cell imaging analysis or flow cytometric analysis after incubation.

* * * * *